US011697837B2

(12) United States Patent
Otwinowski et al.

(10) Patent No.: US 11,697,837 B2
(45) Date of Patent: Jul. 11, 2023

(54) EFFICIENT SEQUENCING OF DSDNA WITH EXTREMELY LOW LEVEL OF ERRORS

(71) Applicant: Board of Regents, The University of Texas System, Austin, TX (US)

(72) Inventors: Zbyszek Otwinowski, Dallas, TX (US); Dominika Borek, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 303 days.

(21) Appl. No.: 17/029,056

(22) Filed: Sep. 23, 2020

(65) Prior Publication Data

US 2021/0002711 A1 Jan. 7, 2021

Related U.S. Application Data

(63) Continuation of application No. PCT/US2019/023931, filed on Mar. 25, 2019.

(60) Provisional application No. 62/647,623, filed on Mar. 23, 2018.

(51) Int. Cl.
*C12Q 1/6813* (2018.01)
*C12Q 1/6869* (2018.01)
*C12N 15/10* (2006.01)

(52) U.S. Cl.
CPC ....... *C12Q 1/6813* (2013.01); *C12N 15/1003* (2013.01); *C12Q 1/6869* (2013.01); *C12N 2310/122* (2013.01)

(58) Field of Classification Search
CPC ............... C12Q 1/6813; C12Q 1/6869; C12Q 1/6855; C12Q 2525/191; C12Q 2525/301; C12N 15/1003; C12N 2310/122
See application file for complete search history.

(56) References Cited

U.S. PATENT DOCUMENTS

| | | | |
|---|---|---|---|
| 5,747,298 A | 5/1998 | Hong et al. | |
| 9,752,189 B2 | 9/2017 | Erlich et al. | |
| 10,392,658 B2* | 8/2019 | Bowen | G01N 27/44721 |
| 2009/0298075 A1 | 12/2009 | Travers et al. | |
| 2015/0044687 A1 | 2/2015 | Schmitt et al. | |
| 2016/0281159 A1* | 9/2016 | Brown | G01N 27/44791 |
| 2021/0371924 A1* | 12/2021 | Salk | C12Q 1/6869 |

FOREIGN PATENT DOCUMENTS

| | | |
|---|---|---|
| WO | 2013142389 A1 | 9/2013 |
| WO | 2013181170 A1 | 12/2013 |
| WO | 2015100427 A1 | 7/2015 |
| WO | 2017100441 A1 | 6/2017 |

OTHER PUBLICATIONS

Wei et al. Rapid short-read sequencing and aneuploidy detection using MinION nanopore technology. Genetics (2016) 202:33-44. (Year: 2016).*
International Search Report, Written Opinion, in priority application PCT/US19/23931.
Kinde, I., Wu, J., Papadopoulos, N., Kinzler, K. W., and Vogelstein, B. (2011) Detection and quantification of rare mutations with massively parallel sequencing, Proceedings of the National Academy of Sciences of the United States of America 108, 9530-9535.
Kennedy, S. R., Salk, J. J., Schmitt, M. W., and Loeb, L. A. (2013) Ultra-Sensitive Sequencing Reveals an Age-Related Increase in Somatic Mitochondrial Mutations That Are Inconsistent with Oxidative Damage, PLoS genetics 9, e1003794.
Schmitt, M. W., Kennedy, S. R., Salk, J. J., Fox, E. J., Hiatt, J. B., and Loeb, L. A. (2012) Detection of ultra-rare mutations by next-generation sequencing, Proceedings of the National Academy of Sciences of the United States of America 109, 14508-14513.
Wang, J., Fan, H. C., Behr, B., and Quake, S. R. (2012) Genome-wide single-cell analysis of recombination activity and de novo mutation rates in human sperm, Cell 150, 402-412.
Gundry, M., Li, W., Maqbool, S. B., and Vijg, J. (2011) Direct, genome-wide assessment of DNA mutations in single cells, Nucleic Acids Res. Mar. 2012;40(5):2032-40.
Zong, C., Lu, S., Chapman, A. R., and Xie, X. S. (2012) Genome-wide detection of single-nucleotide and copy-number variations of a single human cell, Science 338, 1622-1626.
Lu, S., Zong, C., Fan, W., Yang, M., Li, J., Chapman, A. R., Zhu, P., Hu, X., Xu, L., Yan, L., Bai, F., Qiao, J., Tang, F., Li, R., and Xie, X. S. (2012) Probing meiotic recombination and aneuploidy of single sperm cells by whole-genome sequencing, Science 338, 1627-1630.
Meyer, M., and Kircher, M. (2010) Illumina sequencing library preparation for highly multiplexed target capture and sequencing, Cold Spring Harbor protocols 2010, pdb prot5448.
Aird, D., Ross, M. G., Chen, W. S., Danielsson, M., Fennell, T., Russ, C., Jaffe, D. B., Nusbaum, C., and Gnirke, A. (2011) Analyzing and minimizing PCR amplification bias in Illumina sequencing libraries, Genome Biology 12, R18.
Nakamura, K., Oshima, T., Morimoto, T., Ikeda, S., Yoshikawa, H., Shiwa, Y., Ishikawa, S., Linak, M. C., Hirai, A., Takahashi, H., Altaf-Ul-Amin, M., Ogasawara, N., and Kanaya, S. (2011) Sequence-specific error profile of Illumina sequencers, Nucleic Acids Res 39, e90.
Travers KJ, Chin CS, Rank DR, Eid JS, Turner SW. A flexible and efficient template format for circular consensus sequencing and SNP detection. Nucleic Acids Res 2010; 38:159e1-8.
Extended European Search Report, in counterpart EP. 19771893.5.

* cited by examiner

*Primary Examiner* — David C Thomas
(74) *Attorney, Agent, or Firm* — Richard Aron Osman

(57) ABSTRACT

DNA is sequenced by: (a) combining dsDNA fragments with Y-adapters and hairpin adapters comprising an affinity-label under conditions wherein the adapters ligate to fragments forming a mixture of fragment inserts flanked by two Y-adapters, a Y-adapter and a hairpin adapter, and two hairpin adapters; and (b) sequencing the selected fragment inserts with sequencing primers selecting for the Y-adapters.

20 Claims, 3 Drawing Sheets

EFFICIENT SEQUENCING OF DSDNA WITH EXTREMELY LOW LEVEL OF ERRORS

INTRODUCTION

The invention is Hairpin-seq—a highly efficient method to achieve a very low level of error (<1 per 1,000,000 positions) in sequencing-by-synthesis. The method relies on the independence of errors on the two strands of each dsDNA molecule, which is combined with a high-signal-to-noise read-out resulting from a novel design of sequencing adapters—affinity-labeled hairpin Y-adapters. The highly efficient approach can be used to measure accurately low level somatic mutations. A level of somatic mutations higher than the background level can be a hallmark of developing cancer or a genetic predisposition to cancer, or a sign of exposure to a mutagen. Our method can be used as a base for clinical diagnostic tests, such as detecting early signs of cancers, monitoring monitor cancer progression or treatment, and aiding cancer treatments, and also in industry to assess the mutagenic potential and safety of various substances, processes and medical procedures.

Relevant Literature includes methods by our group at UT (Twin-Seq: WO2013/181170) and groups at: UW (WO2013142389, US20150044687, U.S. Pat. No. 9,752,189), Twinstrand Biosciences (WO2017100441) and Guardan (WO2015100427).

SUMMARY OF THE INVENTION

The invention provides methods and compositions for next-generation sequencing (NGS) of nucleic acids. We colloquially refer to some embodiments of subject methods as "Hairpin-Seq".

In an aspect the invention provides a method for sequencing DNA comprising: (a) combining dsDNA fragments with Y-adapters and hairpin adapters comprising an affinity-label under conditions wherein the adapters ligate to fragments forming a mixture of fragment inserts flanked by two Y-adapters (YYs), a Y-adapter and a hairpin adapter (hairpins) and two hairpin adapters (dumbells); (b) sequencing the fragment inserts with sequencing primers selecting for the Y-adapters.

In embodiments:
the sequencing is pair-end or long read sequencing; another alternative to pair end-sequencing is to read-through, but less efficient because the longer the read, the lower the read quality;
the mixture comprises about equal Y-adapters and hairpin adapters, wherein resultant ligation products in the mixture are about 1:2:1 and the method further comprises selecting or enriching for labeled fragment inserts prior to the sequencing step.
the mixture comprises surplus of hairpin adapters compared to Y-adapters sufficient to avoid need of a selection step prior to the sequencing step; for example, with a 9:1 ratio (hairpins to Y-adapters) then 81% of the reaction should be dumbbells, 18% will be the product of interest (hairpins) and 1% will be YYs. Although less efficient, changing the ratios, when the amount of DNA is not a limitation, is effective, as it allows one to skip the selection step; of course, the ratios can be changed and 9:1 is only an example;
the Y-adapter length is adjusted to increase or decrease polony density. The ligated construct to be sequenced (hairpin) will form polonies on the flow cell and the size of those polonies depends on the length of the single stranded parts of the Y-adapters. By adjusting the length of this fragment in the Y-adapters, one can pack polonies more efficiently on the flow cell. This embodiment is particularly applicable for flow cells wherein the spacing between the oligos to which the Y-adapters in hairpins have to hybridize will be larger than current standard length constructs permit.

The standard flow cell is densely covered with the oligos/primers covalently attached to the flow cell. The sequencing library is applied to the flow cell in the form of single stranded pieces of DNA that have appropriate sequencing adapters on both sides (complementary to the grafting sequences of the oligos attached to the flow cell). ssDNA strands hybridize to the flow cell adapters and become the template for the synthesis with the polymerase. After synthesis dsDNA molecule is formed but only one ssDNA strand is covalently attached to the flow cell. After synthesis is completed the dsDNA molecule is denatured and the original strand is washed away (because it is not attached). Its copy stays on the flow cell and can reach to the neighboring primers and hybridize with them forming so-called bridge and serving as a template for the next synthesis. The process is repeated until ~1000 strands of one type are formed. At this point bridges are linearized and one type of strands (reverse) are removed. Both adapters on the flow cell and the ends of the linearized strands are blocked. Then the sequencing of the read 1 commences from the primer hybridized close to the blocked 3' end. The similar approach (bridge amplification) is repeated for the second read, after sequencing of the first read finished.

The polony size in this case is correlated with the length of the insert, i.e. longer inserts can reach further into flow cell adapters. Due to larger distance from the initial site of hybridization the polony becomes bigger, so that the longer the insert (dsDNA part of the hairpin construct in our case) the larger the polony size. For very long inserts the concentration of sequencing constructs has to be decreased in bridge amplification to prevent different polonies getting mixed with each other due to their increasing size and also increasing distortions of shape.

Early commercial flow cells (e.g. Illumina) use a non-patterned surface with a significant excess of the flow cell adapters attached very densely, and it is difficult to change density of flow cell primers with this design without compromising the sequencing process. However, with more recent patterned cells, e.g. US20120316086, the patterning can be designed such that the hairpin construct will not form effectively polonies because it will be too short. Our solution is to extend the hairpin adapter in our processes—the one labeled with the biotin. The extension can be done both by extending the stem of this adapter and by extending the bubble in it.

the dsDNA fragments comprise blunt ends, optionally modified by addition of a single-base, e.g. by dA or dT tailing;
the dsDNA fragments comprise nonblunt ends, optionally generated by digestion and partial fill-in;
step (b) further comprises affinity-enriching for hairpins by affinity hybridization and removing unhybridized dumbells;
further comprising amplifying enriched or selected fragments with primers selecting for the Y-adapters, optionally introducing indexing adapters, and optionally performing an additional selection, e.g. with gene-specific probes; this additional selection is typically performed with probes that have higher affinity for the targeted DNA than its own complementary strand; for example, one can use locked nucleic acids or other modified bases that increase the melting temperature of the "new" duplex formed after hybridization in comparison with the melting temperature of the natural duplex;

the Y-adapters comprise bases promoting mispairing, e.g. oxo-G or universal bases such as 5-nitroindole and inosine, at the stem of the Y-adapter sufficient to weaken zipper closing of the hairpin and promote annealing access by a sequencing primer, providing a sequencing step wherein the hairpin is extended by a bubble after polony amplification;

step (c) comprises use of a decoy provided by a tandem repeat extending beyond the hairpin stem to create another target that competes with the formation of the zipper, preferably wherein the decoy is complementary to the part of the hairpin that interacts with the sequencing primer, ensuring that the hairpin cannot efficiently close, such as wherein the decoys are designed for attenuated hybridization with the sequencing primer; extend outside of the region of the sequencing primer; and/or they may be imperfect tandem repeats, such as having imperfect base pairing in the 13 bp region of complementarity, typically 13 bp region, e.g. using G-T base pairing; and/or wherein step (c) comprises hybridizing the sequencing primer partly or fully outside the stem of the hairpin, wherein configuring the sequencing primer to hybridize entirely/mostly outside of the hairpin is straight-forward, at the moderate cost of some extra chemistry-only cycles to go over the stem needed for the ligation reaction.

The invention includes all combinations of recited particular embodiments as if each combination had been laboriously recited.

DETAILED DESCRIPTION OF PARTICULAR EMBODIMENTS

Figure 1:
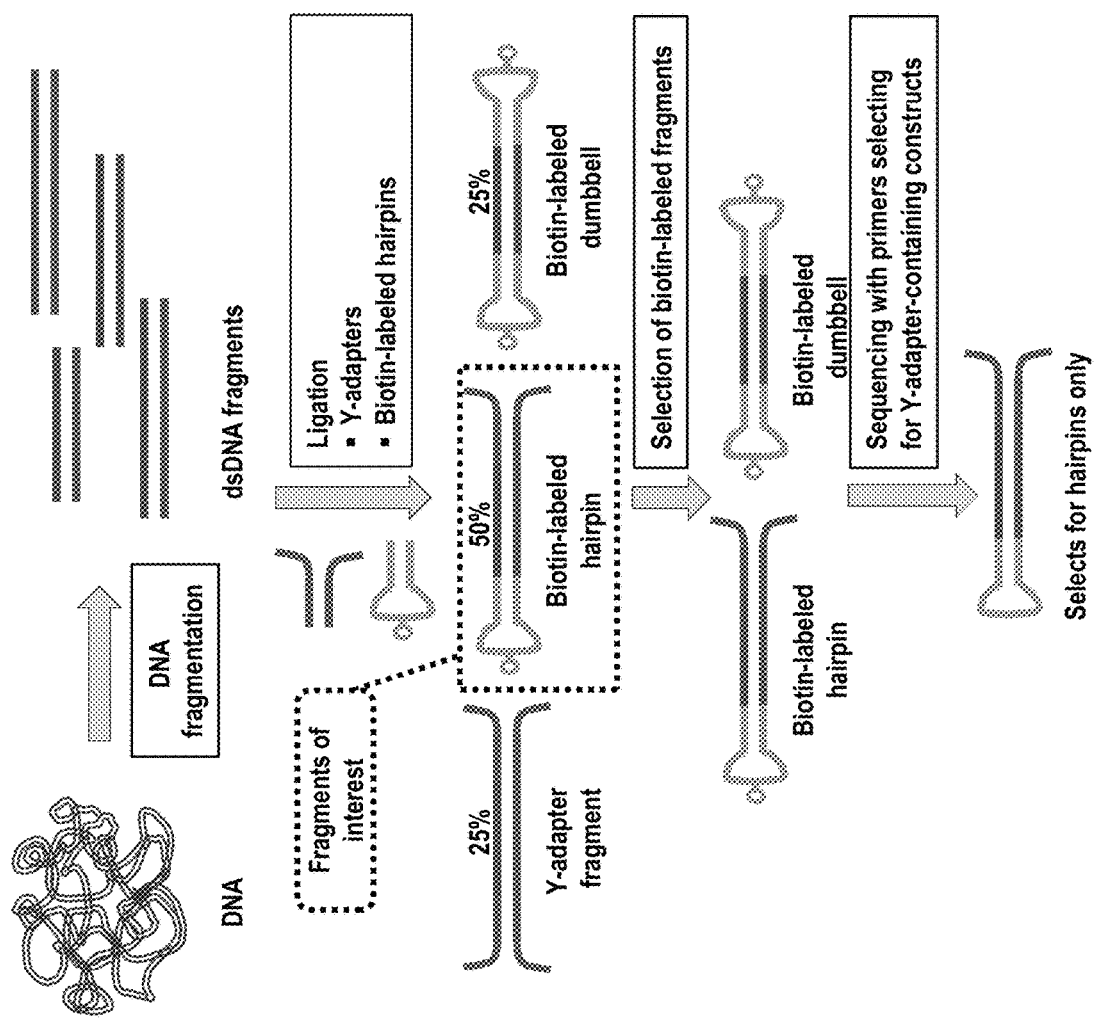
FIG. 1. Schematic representation of Hairpin-seq.

The invention includes all combinations of recited particular embodiments as if each combination had been laboriously recited.

Hairpin-Seq achieves efficient and reliable results by sequencing DNA prepared in the form of hairpins. We fragment DNA using the standard approach, for instance sonication, blunt-end it enzymatically with Mung Bean nuclease to avoid correlated errors, and then perform ligation with an equimolar mix of two adapters: modified Y-adapters and hairpin adapters that will be labeled, e.g. with biotin. Ligation creates a mixture of inserts with two Y-adapters, hairpins, and dumbbells. Double Y-adapters do not contain biotin, while dumbbells do not hybridize to oligonucleotides attached to the flow cell. From the sequencing perspective, dumbbells are simply inert material. After selecting the constructs that contain at least one adapter labeled with biotin, we quantify the Y-adapters by qPCR, in which the dumbbells are also inert. The resulting efficiency of library preparation, which is approximately 50% compared to the theoretical efficiency of the standard approach, is much higher than what is needed for PCR-free methods, and eliminating PCR amplification additionally decreases errors in sequencing.

By several measures our method offers improved efficiency:

(a) How much of sequenced dsDNA library corresponds to productive Twin-seq/Hairpin-seq pairs? We reached only 30% of efficiency for Twin-seq, and the UW methodology efficiency was lower by an order of magnitude. With hairpin-seq we can achieve 66% efficiency (the 25% of original reaction is inert in sequencing) without any selection for our 1 to 1 ratio of adapters. However, by changing the ratios of hairpin to Y-adapters we can increase this efficiency further, e.g. 9:1 hairpin to Y-adapters will give us 81% of dumbbells, 18% of hairpins and 1% of YY constructs. Only hairpins and YY will be sequenced so we will have the efficiency close to 90%. Furthermore, if combined with the selection in both cases (1:1 and 9:1) efficiency should be close to 100% because we will select only Y-hairpin and dumbbells constructs. This efficiency makes the method practical in the experimental sense.

(b) How much of the productive sequencing is lost due to requirement for the clonal amplification in the UW and Twin-seq methods, and in other versions of digital sequencing. This efficiency—how many copies of the dsDNA fragment we have to clonally amplify to be certain is driven by statistical reasoning. The two strands of dsDNA fragment are separated during sequencing in the UW method, in Twin-seq, and in other similar methods; hence, one needs to have 6-10 clonal copies of each strand to be certain that they belong to the same clonal cluster. This means that the efficiency is only 10-15% because instead of 100% of unique dsDNA, we sequence 10-15% of unique dsDNA. The 85-90% represents the copies of 10-15%. Here, because we have two ssDNA copies entering the sequencing together, our efficiency increases to 50%. This level is not affected by the efficiency (a) if the selection is used.

(c) How much dsDNA material is not entering the sequencing because it is not ligated or because it forms non-productive constructs? This measure of efficiency—how much material will lead to unproductive constructs that will not be sequenced with hairpin-seq. With ratio 1:1 for YY and hairpin adapters only 50% of material will form constructs flanked with Y and hairpin adapters, and 25% of constructs will have YY adapters, while the ratio 1:9 for YY and hairpin adapters, only 18% will form the constructs of interest. While we will lose initial material, this efficiency is not the issue, as the amount of DNA is rarely the limitation. Our hairpin seq increased efficiencies of converting dsDNA to productive constructs that provide information about the complementary strands and decreasing the need for the clonal amplification. Combining the efficiency gains of (a) and (b) our method has efficiency one to two orders of magnitude higher than current methods.

Hairpin-seq is unique in that it always reads both strands from the original DNA in paired-end sequencing. Additionally, with read lengths shorter than the stem of the hairpin, the efficiency of observing corresponding positions together is 100% (FIG. 2).

FIG. 1 is a schematic representation of Hairpin-seq. The Y-adapters are modified (herein), but for simplicity modifications are not shown.

Figure 2:
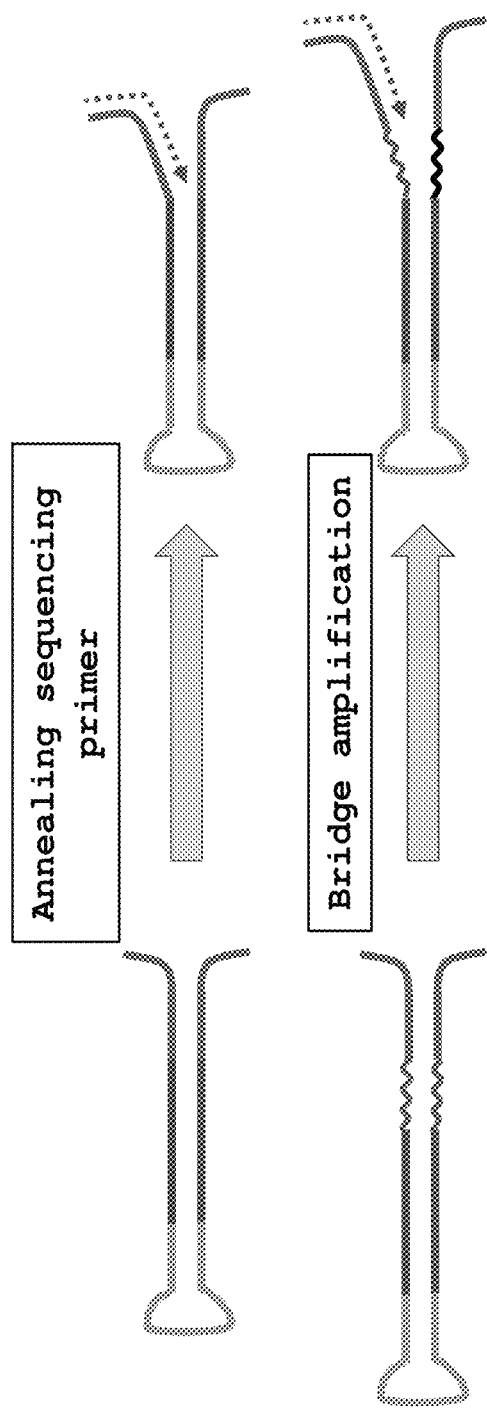
FIG. 2: Schematic representation of the zipper-closing problem.

FIG. 2 is a schematic representation of the zipper-closing problem. Annealing of the sequencing primer to the ssDNA fragments on the flow cell requires the hairpins to be unzipped. However, in standard conditions of sequencing, zipper closing will be kinetically favored over the annealing of the sequencing primer. To solve this problem we introduce universal bases or bases promoting alternative pairing efficiently before bridge or PCR amplification to obtain regions of lower propensity for forming zippers extending beyond the standard sequence to which the sequencing adapter anneals. If PCR is used, we introduce them before PCR amplification and PCR amplifications generate variability, so if this is PCR-free, then we introduce them before the bridge amplification. The universal bases are introduced in the ligation adapters, just after standard sequence to which sequencing adapters anneals, After the sequencing primer is annealed a strand-displacing polymerase can proceed without the zipper-closing problem. The lower left panels shows introducing the universal bases 5-nitroindole and inosine, so that the effect of zipper-closing is weakened; and the lower right panel shows that after bridge amplification, the sequence forming hairpin will have a stretch of bases that will not form a duplex or will have weaker base-pairing interactions, for instance interactions of G to T or other non-standard pairings, which will help to anneal the sequencing primer; i.e. the result can be achieved with non-standard base pairings or with standard bases.

One of the core reasons Hairpin-seq is so inventive comes from analyzing the artifacts of sporadic ligation in normal library preparation, which results in the same type of hairpins as the ones we use in Hairpin-seq. The sequencing quality of such hairpins is much lower than for other reads, so even a proposal like Hairpin-seq would appear technically dismissable. The lower quality of hairpin reads has been reported for non-artificial hairpins that are sometimes formed by inverted genomic repeats during sequencing. However, our detailed analysis, made possible only by inspecting fluorescence intensities, revealed that the problems with the sequencing quality of hairpins formed by inverted repeats and those hairpins that we use here result from two different mechanisms. Hairpins formed by inverted repeats have good total fluorescence intensity, but the quality of the readout associated with them is sometimes affected by phasing. The Hairpin-seq structures, on the other hand, have on average very low fluorescence intensities from the start of the read, most frequently about 5-10 times weaker than non-hairpin reads (FIG. 3).

Figure 3:
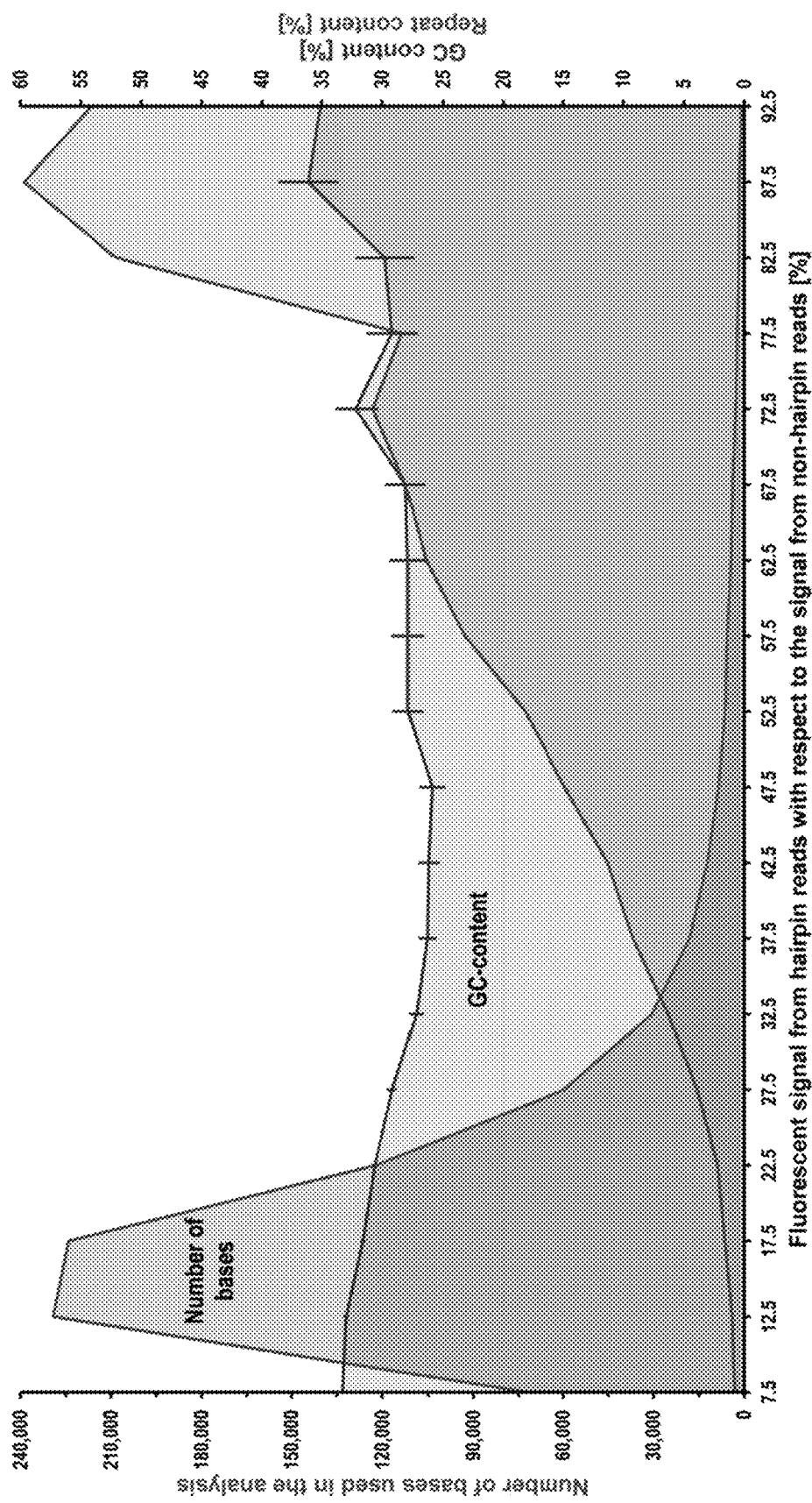
FIG. 3: The dependence of the strength of the fluorescence signal on different types of hairpins.

FIG. 3 shows the dependence of the strength of the fluorescence signal on different types of hairpins. The blue area shows how many hairpin bases have been used in data analysis. The brown area shows the GC content plotted as a function of the strength of fluorescence signal. The orange area shows how the presence of tandem repeats correlates with an increase in fluorescence, which indicates that the fluorescence signal strength depends on the initial hybridization of the sequencing primer. The orange color represents a fraction of hairpin sequencing reads, in which tandem repeats have been detected. The fraction of reads with tandem repeats increases with the increase of the fluorescent signal. Stems of hairpins with the weak fluorescence signals contain more GC than stems of hairpins with intermediate levels of fluorescence signal. This indicates that weak hybridization of the sequencing primer contributes to loss of fluorescence. These differences are significant due to the very high counting statistics for these GC-content ratios.

Many characteristics of these hairpins point to inefficient initiation of DNA synthesis during the sequencing due to the zipper-closing effect of the hairpin out-competing the hybridization of the sequencing primer (FIG. 2). Correlations presented in FIG. 3 confirm this mechanism; the stronger zippers (with higher GC content) compete better, while the presence of a decoy provided by a tandem repeat extending beyond the hairpin stem creates another hybridization target that competes with the formation of the zipper, thereby increasing the hybridization of the sequencing primer. Therefore, in embodiments we modify the Y-adapter and/or the sequencing primers, so that the hybridization frequency will increase, by decreasing the zipper-closing propensity of the constructs, which improves the fluorescence signal to a level consistently similar to non-hairpin reads. Illumina sequencing allows for the addition of custom sequencing primers, which is considered a standard feature—for example, when using different types of custom-designed libraries mixed together. In embodiments we reconfigure the Y-adapters and one or both sequencing primers. One embodiment hybridizes the sequencing primer outside the stem of the hairpin. This imposes a cost of wasting the initial 13 sequencing cycles. One can perform these cycles using so-called 'dark cycles', applying the chemistry without the readout step. This improves the speed but does not reduce the cost of sequencing. Alternatively, one can take advantage of the difference in the stability of the hairpin in the experimental conditions of ligation and sequencing initiation, for instance due to the difference in temperature used at these steps. Ligation requires a dsDNA substrate; however, it well accepts variations in base-pairing outside the first four proximal bases, and can accept modified bases even within this 4 base-pair stem. In embodiments we employ universal bases, such as 5-nitroindole and inosine, and introduce them at the stem of the Y-adapter. They form dsDNA suitable for ligation, but on the flow cell, when the polony is formed by bridge amplification, the replicating polymerase will introduce mismatches, which decreases the propensity for zipper-closing. To additionally weaken the zipper, we can introduce non-standard pairing, e.g. G-T, in the double-stranded part of the Y-adapter, and modify the sequencing primers accordingly.

EXAMPLES

Hairpin-Seq can transform NGS methods so that the produced results are reliable enough to allow for the analysis of subclonal mutations, while the efficiency, in terms of the costs of sequencing and sample quantity, is not sacrificed.

Our Hairpin-seq method can outperform other approaches[1-7], including duplex sequencing[3], by one or more orders of magnitude in terms of reliability and efficiency. The reliability approaching one error per billion base pairs in combination with the high efficiency of sequencing would be undeniably recognized as a major technological advance by researchers in the sequencing field, in particular when they consider that we plan to achieve this goal relying on mainstream hardware. Particular applications include areas that use NGS as a tool, but are hindered by the technical limitations of current sequencing approaches. Our methods enable broad studies on many subjects, for instance: (1) the somatic evolution of cancer, by providing data on subclonal mutations, the role of mismatch repair and DNA break repair, and mutator phenotypes in cancer treatment; (2) aging, by providing data on how mutational rates and spectra depend on age and environmental factors; (3) the mutagenic potential of environmental insults, iatrogenic procedures, food supplements and other sources, which can result in new types of epidemiological research. This will guide a broad range of preventive strategies, which now, due to the lack of reliable data, are often controversial, and may have high costs and uncertain benefits.

Hairpin-seq combines several innovative ideas. In the experimental part of Hairpin-seq, redundant information regarding the sequences of two complementary strands of a DNA fragment is retrieved by paired-end sequencing of the stems of hairpins that are generated during sequencing library preparation. Such an approach results in 100% efficiency of retrieving redundant, complementary sequences, which leads to productivity ~50× higher than reported in the published results[3]. However, the idea of using hairpins in sequencing can be easily dismissed due to the misperception that hairpins interfere with Illumina sequencing quality, since their presence has been correlated with low quality results[8-10]. Our more detailed analysis, which took into account the strand-displacing property of the polymerases used in sequencing[11], revealed that structures more complex than hairpins are affected by polymerase elongation, while for hairpins, the hybridization of sequencing adapters is the main problem. In this application, we provide solutions to the hybridization problem so that we can fully capitalize on the gain from the independent information present in hairpin constructs.

REFERENCES

[1] Kinde, I., Wu, J., Papadopoulos, N., Kinzler, K. W., and Vogelstein, B. (2011) Detection and quantification of rare mutations with massively parallel sequencing, Proceedings of the National Academy of Sciences of the United States of America 108, 9530-9535.

[2] Kennedy, S. R., Salk, J. J., Schmitt, M. W., and Loeb, L. A. (2013) Ultra-Sensitive Sequencing Reveals an Age-Related Increase in Somatic Mitochondrial Mutations That Are Inconsistent with Oxidative Damage, PLoS genetics 9, e1003794.

[3] Schmitt, M. W., Kennedy, S. R., Salk, J. J., Fox, E. J., Hiatt, J. B., and Loeb, L. A. (2012) Detection of ultra-rare mutations by next-generation sequencing, Proceedings of the National Academy of Sciences of the United States of America 109, 14508-14513.

[4] Wang, J., Fan, H. C., Behr, B., and Quake, S. R. (2012) Genome-wide single-cell analysis of recombination activity and de novo mutation rates in human sperm, Cell 150, 402-412.

[5] Gundry, M., Li, W., Maqbool, S. B., and Vijg, J. (2011) Direct, genome-wide assessment of DNA mutations in single cells, Nucleic Acids Res.

[6] Zong, C., Lu, S., Chapman, A. R., and Xie, X. S. (2012) Genome-wide detection of single-nucleotide and copy-number variations of a single human cell, Science 338, 1622-1626.

[7] Lu, S., Zong, C., Fan, W., Yang, M., Li, J., Chapman, A. R., Zhu, P., Hu, X., Xu, L., Yan, L., Bai, F., Qiao, J., Tang, F., Li, R., and Xie, X. S. (2012) Probing meiotic recombination and aneuploidy of single sperm cells by whole-genome sequencing, Science 338, 1627-1630.

[8] Meyer, M., and Kircher, M. (2010) Illumina sequencing library preparation for highly multiplexed target capture and sequencing, Cold Spring Harbor protocols 2010, pdb prot5448.

[9] Aird, D., Ross, M. G., Chen, W. S., Danielsson, M., Fennell, T., Russ, C., Jaffe, D. B., Nusbaum, C., and Gnirke, A. (2011) Analyzing and minimizing PCR amplification bias in Illumina sequencing libraries, Genome biology 12, R18.

[10] Nakamura, K., Oshima, T., Morimoto, T., Ikeda, S., Yoshikawa, H., Shiwa, Y., Ishikawa, S., Linak, M. C., Hirai, A., Takahashi, H., Altaf-Ul-Amin, M., Ogasawara, N., and Kanaya, S. (2011) Sequence-specific error profile of Illumina sequencers, Nucleic Acids Res 39, e90.

[11] U.S. Pat. No. 5,747,298, U. S. p. (2011) Bst DNA polymerase with proof-reading 3'-5' exonuclease activity.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

What is claimed is:

1. A method for sequencing DNA comprising:
   a) combining double-stranded DNA (dsDNA) fragments with: (i) Y-adapters each comprising a stem and (ii) hairpin adapters comprising an affinity-label, under conditions wherein at least some of the Y-adapters and at least some of the hairpin adapters ligate to at least some of the fragments forming a mixture of fragment-adapter complexes comprising:
      fragment inserts flanked by two Y-adapters ("YY complexes"),
      fragment inserts flanked by a Y-adapter on one end and a hairpin adapter on the other end ("hairpin complexes"), and
      fragment inserts flanked by two hairpin adapters ("dumbbell complexes"); and
   b) sequencing the fragment inserts of the hairpin complexes with sequencing primers selecting for the Y-adapters,
   wherein the Y-adapters comprise bases promoting mispairing at the stem of the Y-adapter sufficient to weaken zipper closing at the stem and promote annealing access by a sequencing primer.

2. The method of claim 1 wherein the sequencing step comprises bridge or PCR amplification to obtain regions of lower propensity for forming zipper closing that extends beyond a sequencing primer binding sequence.

3. The method of claim 1 wherein the bases promoting mispairing are selected from oxo-G, 5-nitroindole, and inosine.

4. The method of claim 2 wherein the bases promoting mispairing are selected from oxo-G, 5-nitroindole, and inosine.

5. The method of claim 2 wherein the sequencing step comprises extending the hairpin by a bubble after polony amplification.

6. The method of claim 1 wherein the sequencing is paired-end or long read sequencing.

7. The method of claim 1 wherein the combining step comprises combining the fragments with a mix of about equal Y-adapters and hairpin adapters, wherein resultant ligation products in the mixture are about a 1:2:1 ratio of the YY complexes, the hairpin complexes, and the dumbbell complexes, and wherein the method further comprises selecting or enriching for complexes comprising the affinity-label prior to the sequencing step.

8. The method of claim 1 wherein the combining step comprises combining the fragments with a mix of a surplus of hairpin adapters compared to Y-adapters.

9. The method of claim 1 wherein the dsDNA fragments comprise blunt ends.

10. The method of claim 1 wherein the dsDNA fragments comprise nonblunt ends.

11. The method of claim 1 wherein step (b) further comprises affinity-enriching for complexes including at least one hairpin adapter.

12. The method of claim 1 further comprising amplifying enriched or selected fragments with primers selecting for the Y-adapters.

13. The method of claim 1 wherein step (b) comprises use of a tandem repeat extending beyond the stem to create a target that competes with zipper closing.

14. The method of claim 2 wherein step (b) comprises use of a tandem repeat extending beyond the stem to create target that competes with zipper closing.

15. The method of claim 1 wherein step (b) comprises use of a tandem repeat extending beyond the stem to create another target that competes with zipper closing, wherein the tandem repeat is complementary to the part of the Y-adapter that interacts with the sequencing primer, such that the complex cannot efficiently close.

16. The method of claim 2 wherein step (b) comprises use of a tandem repeat extending beyond the stem to create a target that competes with zipper closing, wherein the tandem repeat is complementary to the part of the Y-adapter that interacts with the sequencing primer, such that the complex cannot efficiently close.

17. The method of claim 1 wherein step (b) comprises use of a tandem repeat extending beyond the stem to create a target that competes with zipper closing, wherein the tandem repeat provides attenuated hybridization with the sequencing primer and extends outside of a region of primary sequencing primer binding.

18. The method of claim 2 wherein step (b) comprises use of a tandem repeat extending beyond the stem to create a target that competes with zipper closing, wherein the tandem repeat provides attenuated hybridization with the sequencing primer and extends outside of a region of primary sequencing primer binding.

19. The method of claim 1 wherein step (b) comprises use of a tandem repeat extending beyond the stem to create a target that competes with zipper closing, wherein the tandem repeat comprises imperfect base pairing in a region of complementarity in the stem.

20. The method of claim 1 wherein step (b) comprises hybridizing the sequencing primer partly or fully outside the stem.

* * * * *